United States Patent [19]

Pawelek et al.

[11] Patent Number: 4,508,706

[45] Date of Patent: Apr. 2, 1985

[54] COMPOSITION FOR INCREASING MELANIN IN MAMMALIAN SKIN AND HAIR

[75] Inventors: John M. Pawelek, Hamden, Conn.; Patricia P. Agin, Cordova, Tenn.

[73] Assignees: Yale University, New Haven, Conn.; Plough, Inc., Memphis, Tenn.

[21] Appl. No.: 480,465

[22] Filed: Mar. 30, 1983

[51] Int. Cl.³ .................... A61K 7/44; A61K 31/66
[52] U.S. Cl. .................................... 424/60; 514/107; 514/110
[58] Field of Search ............... 424/59, 60, 206, 209, 424/211; 260/930, 936, 941

[56] References Cited

U.S. PATENT DOCUMENTS

| | | | |
|---|---|---|---|
| 2,949,403 | 8/1960 | Andreadis et al. | 424/60 |
| 4,021,538 | 5/1977 | Yu et al. | 424/60 |
| 4,228,151 | 10/1980 | Lang et al. | 424/60 |
| 4,293,542 | 10/1981 | Lang et al. | 424/60 X |

*Primary Examiner*—Sam Rosen
*Assistant Examiner*—Shawn P. Foley
*Attorney, Agent, or Firm*—Gerald S. Rosen; Thomas D. Hoffman

[57] ABSTRACT

A composition and method useful for increasing the accumulation of melanin in the skin of humans and other mammals wherein the composition comprises at least one O-phosphorylated derivative of 3-(3,4-dihydroxy)phenylalanine.

23 Claims, No Drawings

COMPOSITION FOR INCREASING MELANIN IN MAMMALIAN SKIN AND HAIR

FIELD OF THE INVENTION

This invention relates to the coloration of mammalian skin. More particularly it relates to a composition which increases the natural accumulation of melanin in the skin of humans and other mammals thereby imparting to the skin a natural tan or coloration and a method for increasing said melanin accumulation.

BACKGROUND

Melanins are a class of structurally related chemicals which are the principal pigments of mammalian skin and hair. Melanins are synthesized by specialized cells termed "melanocytes" or "pigment cells", which are found in the skin and hair follicles. Melanocytes respond to ultraviolet radiation, for example, that found in sunlight, by going through cell divisions and by producing more melanin. The net result of exposure to ultraviolet radiation is therefore an increase in the number of melanocytes and an increase in melanin content of the skin. This entire process is known commonly as "sun tanning." The ability of human beings to sun-tan is of great medical significance because it has been well-documented that light-skinned individuals are much more susceptible to sun-induced skin cancers than are dark-skinned individuals. Sun-tanning is also of great social significance in that in many parts of the world increased melanin pigmentation is aesthetically desirable. However, for many individuals sun-tanning is difficult to achieve without concomitant erythema (i.e., sunburn) and resultant peeling of the skin.

Other individuals are unable to achieve an acceptable sun tan due to their being afflicted with vitiligo which is a disorder of unknown origin which results in the acquired loss of melanocytes in various areas of the skin. The net result of vitiligo is, in the extreme, total depigmentation of skin and hair. More commonly, vitiligo results in patchy white areas of the skin and hair. In dark-skinned individuals vitiligo can cause severe cosmetic problems and resultant psychological stress. Vitiligo afflicts about 1% or 40 million, of the world's population. A prime treatment for vitiligo is with psoralens and ultraviolet radiation which results in an increase in the number of melanocytes and melanin production in the patchy white areas of the skin. However, psoralens are toxic—causing dermatitis and necrosis when applied to the skin and hepatic insufficiency and nervous and digestive disorders when ingested. There is also evidence that psoralens pklus ultraviolet light will induce skin cancer.

Thus, it has long been desired to find a means of effecting an increased accumulation of melanin in the skin and hair of humans and other mammals without the concomitant disadvantages described above, e.g., erythema and/or skin cancer or other toxic effects.

In order to avoid the aforementioned disadvantages of exposure to the sun, it has been proposed to use solar filters (i.e. sun screening agents) whereby the amount of erythema causing radiation reaching the skin is diminished. However, in some cases the sun screening agents reduce the total amount of radiation to the point where the rate of tanning is decreased to an undesirably low level. Thus, many persons desiring a rapid tan are discouraged from using sun screens.

In an attempt to achieve a tanning effect without the above-indicated disadvantages of exposure to UV irradiation and without the use of solar filters in U.S. Pat. No. 2,949,403, for example, it has been proposed to use a composition comprising dihydroxyacetone to effect a "simulated" tan on the skin. This composition by effecting the so-called tan through its reaction with the proteinaceous components of the skin obviates the need for exposure to the sun thereby preventing the deleterious effects of such exposure as defined above. However, use of the above composition suffers from numerous disadvantages. It frequently results in different shadings on the skin due to uneven application. Furthermore, the colored areas are non-uniformly removed during cleaning of the skin.

A number of compositions useful for enhancing coloration of the skin due to exposure to the sun have been proposed in e.g., U.S. Pat. No. 4,293,542 wherein pyridinyl oxide derivatives are disclosed which function at UV wavelengths outside the erythemal range thus permitting use of sun-screening agents while facilitating rapid tanning without the usual concomitant effects of exposure to the shorter UV wavelengths.

In U.S. Pat. No. 4,228,151 there are disclosed various quinoxaline derivatives which may be used in a similar manner. However, the above compositions require that melanocytes be present in the epidermis in order that exposure to UV radiation be able to effect the coloration of the epidermis. If, however, such melanocytes are not present in the epidermis tanning or melanization can not occur despite administration of the aforementioned composition and exposure to UV radiation. Thus, persons having low, or no, concentrations of melanocytes in the epidermis (e.g., vitiligo victims) could not achieve melanization of the epidermis by using the compositions disclosed in the prior art.

Furthermore, in U.S. Pat. No. 4,021,538 there are described compositions for "producing pigmentation in . . . skin" comprising the salts of aliphatic esters of DOPA or α-methyl DOPA. In order to effect the desired pigmentation the above salts must be oxidized, in alkaline media prior to topical application to the subject or by in vivo oxidation by means of topical application of additional oxidizing agents.

The present invention provides compounds useful in preparing compositions which increase the number of melanocytes and the production of melanin in mammalian skin even in the absence of exposure to UV radiation.

It has now been found, in accordance with this invention, that increased natural melanization of the epidermis can be achieved without adverse effects, even in persons having no epidermal melanocytes, by administering to such persons the composition according to the instant invention in the absence of exposure to UV radiation.

SUMMARY OF THE INVENTION

The present invention provides compounds useful in preparing compositions which increase the number of melanocytes and the production of melanin in mammalian skin even in the absence of exposure to radiation.

The invention further provides compounds useful in the preparation of a composition which increases production of melanin in the epidermis of humans and other mammals even when melanocytes were originally absent.

There is also provided by the invention methods for increasing the number of melanocytes and the production of melanin in the epidermis of humans and other mammals even when melanocytes were originally absent and even in the absence of exposure to UV radiation.

DETAILED DESCRIPTION OF THE INVENTION

Thus, in accordance with this invention there is provided a composition for increasing epidermal melanocyte and melanin production comprising an O-phosphorylated derivative of DOPA (hereinafter "PD") comprising a compound of the general formula I

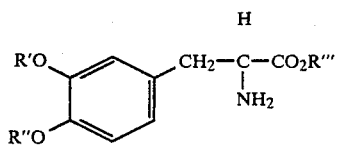

wherein R' and R" each represent hydrogen or

or R' and R" together represent

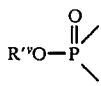

wherein R'$^v$ and R'" each represent hydrogen or a pharmaceutically acceptable cation; with the provisos that R' and R" cannot both be hydrogen.

More particularly preferred O-phosphorylated derivatives of DOPA useful in accordance with this invention are those of the formulae II to IV below

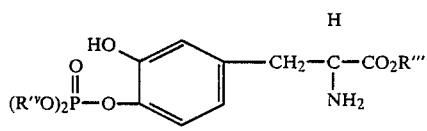

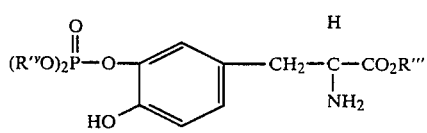

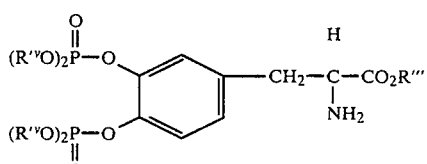

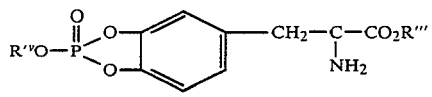

wherein R'" and R'$^v$ are as defined above.

The advantage of the above compounds lies in their greater stability and solubility compared to DOPA itself which is a precursor to melanin. The O-phosphorylated derivatives may be made by known methods such as reaction of DOPA with phosphorous oxychloride followed by hydrolysis, treatment with polyphosphoric acid and treatment with polyphosphoric acid or a mixture of phosphoric acid and phosphorus pentoxide. Preferred methods for preparing the compound according to the invention are treatment with polyphosphoric acid or a mixture of phosphoric acid and $P_2O_5$. In a preferred embodiment the compounds of the instant invention are prepared from L-DOPA.

The desired compounds are then isolated in the forms of their free acids or salts.

The salt forms which are most useful in accordance with the invention are those where the cations are pharmaceutically acceptable cations selected from the group consisting of metal cations, both mono- and polyvalent, triethanolamine, tris(hydroxymethyl)aminomethane, and similar cations which are not readily oxidized or reduced.

Illustrative of the metal cations which are useful in accordance with the invention are sodium, potassium, calcium and magnesium, and the like. Easily oxidized or reduced cations which may not be used in the practice of the invention include those of iron and copper. Preferred cations for use in accordance with the invention include the non-oxidizable and non-reducible cations such as those from triethanolamine, tris(hydroxymethyl)aminomethane, sodium and potassium.

Furthermore, in the event that the composition is to be administered orally or parenterally the choice of cation will depend upon the subject's medical history. E.g., if the subject is on a salt-free diet the cation should not be sodium.

In accordance with another embodiment of the invention there is provided a composition for increasing melanization in mammalian epidermis comprising an admixture of (a) an effective amount of at least one O-phosphorylated derivative of DOPA of the general formula I

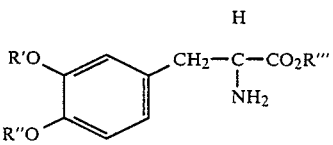

wherein R' and R" each represent hydrogen or

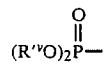

or R' and R'" together represent

wherein R'$^v$ and R''' each represent hydrogen or a pharmaceutically acceptable cation; with the provisos that R' and R'' can not both be hydrogen.

Most preferred compounds of the formulae I through V are those prepared from L-DOPA.

Preferred compounds of the formula I, for use according to the invention are those of formulae II to V below and mixtures thereof:

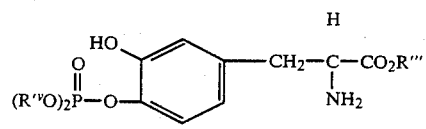

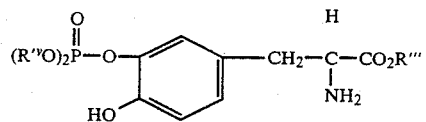

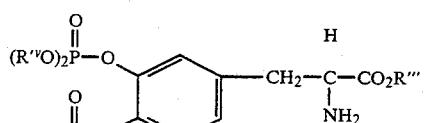

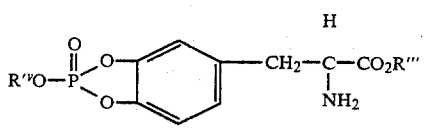

wherein R''' and R'$^v$ are as defined above.

Pharmaceutically acceptable carriers useful in the practice of the invention are known in the art and include, for injection—distilled water; for controlled release—microcapsules comprising carboxymethylene copolymers; for transdermal release—acrylamides and for topical applications—cosmetic bases.

In addition, if desired, the composition according to this embodiment comprises at least one additive selected from the group consisting of solvents, fragrances, sunscreening agents, preservatives, and chelating agents.

Furthermore, as compositions for use in accordance with the embodiment of the invention must be physiologically acceptable it may be necessary to convert the O-phosphorylated DOPA derivatives, if obtained in their free acid form, to their salt forms, e.g., by ion exchange or to add acids, bases or buffers to obtain compounds having the required acidity characteristics. Such methods, acids, bases, and buffers are known, per se, and will not be discussed further.

Cosmetic bases useful in the practice of the invention are well known and include lotions, creams, ointments, and dusting powders. Examples thereof may be found in e.g., U.S. Pat. Nos. 4,228,151; 4,282,206 and 2,949,403.

Solvents for use in accordance with the invention include ethanol, distilled and/or deionized water, physiological saline solution and the like. The specific solvent chosen will depend on the method of application.

Fragrances useful in the preparation of compositions for tanning or sun-tanning are known, per se, and will not be discussed further.

As the O-phosphorylated DOPA derivatives are good microbiological growth media it is also desirable to add a preservative to compositions comprising those materials if they are to be used for topical applications.

Preservatives are well known and may be exemplified by methylparaben, Dowacil ™ 2000 and propylparaben.

Sunscreening agents for topical use in accordance with the invention include most commercially available screening agents especially those described by the Monograph On Sunscreens, Fed. Register, Part 2, 43 (Aug. 25, 1978) as safe and effective. Additional sunscreening agents are described e.g., in U.S. Pat. Nos. 4,264,581; 2,949,403 and 4,256,664.

As compositions comprising the O-phosphorylated DOPA derivatives may be deactivated by reducible or oxidizable cations, such as those of copper or iron, or even by excess amounts of multivalent cations such as calcium or magnesium it is often desirable to have such compositions contain chelating agents, many of which are known in the art, such as ethylenediaminetetraacetic acid (EDTA).

If desired, in order to reduce the acidity or basicity of the compositions, bases, acids or buffers may be added thereto in accordance with the knowledge of the art.

In accordance with yet another embodiment of the invention there is provided a method of increasing epidermal malanization in humans and other mammals comprising the steps of applying to said human or mammal a composition comprising an admixture of an effective amount of (a) at least one O-phosphorylated DOPA derivative of the general formula I

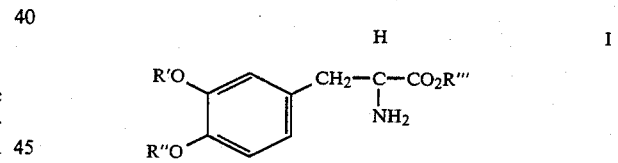

wherein R' and R'' each represent hydrogen or

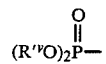

or R' and R'' together represent

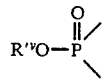

wherein R'$^v$ and R''' each represent hydrogen or a pharmaceutically acceptable cation with the provisos that R' and R'' can not both be hydrogen.

It has also been found in accordance with another modification of the above embodiement of the invention that the extent of melanization may be intensified if the subject is also exposed to UV irradiation prior to and during application of the melanization increasing composition.

Preferred O-phosphorylated compounds for use in accordance with this embodiment of the invention are compounds of the formulae II to V below:

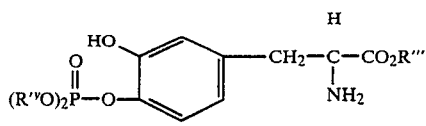

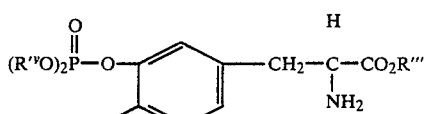

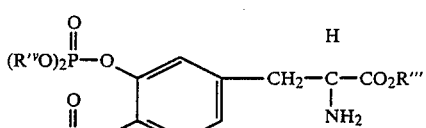

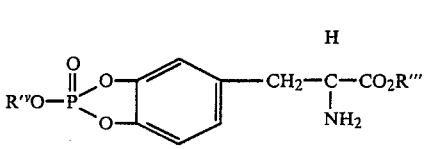

wherein $R'''$ are $R'^v$ are as defined above.

Most preferred compositions which are useful in the practice of the invention are those in which the compounds of formulae I through V are derived from L-DOPA.

In addition the compositions useful in accordance with the invention may comprise at least one additive selected from the group consisting of solvents, fragrances, sunscreening agents, preservatives and chelating agents, and the like as described above.

In accordance with the above embodiment of the invention there is also provided a method of imparting a "tan" coloration to a subject even one having a low concentration of epidermal melanocytes for instance subjects suffering from vitiligo.

The O-phosphorylated DOPA derivatives are usually present in the melanization increasing compositions in concentrations, based on the total composition, of about 0.005 to about 1.0% wt. A preferred concentration of O-phosphorylated DOPA derivatives is about 0.017% wt.

The following examples are merely illustrative and are not meant to limit the scope of the invention which is defined by the appended claims.

Throughout the following examples one parts by weight refer to grams and parts by volume to millileters.

EXAMPLE 1

A. Preparation of O-phosphorylated DOPA derivative (PD)

(a) To 8.2 ml. of concentrated phosphoric acid were slowly added, with stirring, 8.4 gms of $P_2O_5$. Stirring of the above mixture was continued until a homogeneous solution was obtained.

(b) To the above mixture was then added 3 gms of L-DOPA and the resultant mixture stirred until the DOPA dissolved.

(c) The solution from (b) was heated, with stirring, at 100° C. for 72 hours during which the solution darkened in color.

(d) The above dark solution was then poured over 130 ml. of ice and after thawing and mixing, the resulting mixture was poured into a chromatographic column (of approximately 6×60 cm.) containing Dowex TM 50W-X8 (Biolab, Inc.), of 200-400 mesh, which had been equilibrated with water. The O-phosphyrylated DOPA is retained on the column while the excess $H_3PO_4$ and inorganic salts pass through the column quickly. After elution of the $H_3PO_4$ and inorganic salts the pH of the solution rises. The O-phosphorylated DOPA, as detected by its UV absorption at 280 nm, is then eluted.

(e) The O-phosphorylated DOPA is then recovered from the pooled eluates, showing absorption at 280 nm, by lyophilization. The O-phosphorylated DOPA was then purified by passage through a chromatographic column containing Dowex TM AG1-X8 (VBio-Rad Co.), of 200-400 mesh, in the chloride form which has been equilibrated with water. It is then eluted with an HCl gradient of about 0 to 150 mm. The eluates, showing a peak at 280 nm, are pooled and lyophilized whereby the desired product (hereinafter "PD") is obtained.

B. Melanization of mouse epidermis using the O-phosphorylated DOPA derivative

Eight groups of Skh-2 pigmented hairless mice, having no epidermal melanin, (6/group) were painted with a solution of the composition of part A in 0.1M Tris TM - 25% glycerol buffered at a pH of 7.0. The concentrations of the DOPA derivatives ranged between about 0.005 and about 1.0% wt. Painting, on the dorsal skin of the mice, at a daily rate of 2 $\mu l/cm^2$ was effected for 2 weeks. Four of the groups were also subjected to UV irradiation, using a filtered FS-20 UV lamp for 10 min/day, three days per week for a total of four weeks. During the irradiation course the painting of the mice skin continued as described above. Liver and brain tissues, as well as skin, were examined histologically. One group of mice was only subjected to irradiation as a control. It was found that melanization in the mice treated with the PD alone was greater than in the mice treated only by irradiation. Irradiation, in addition to the treatment with PD, increased the intensity of the melanization.

The following examples describe formulation for use in administration to the subject in accordance with the various methods indicated above.

EXAMPLE 2

Injectable composition

A solution was prepared by mixing 500 mg. by weight of PD, in the form of its sodium salt, with sufficient sterile water to prepare 2 parts by volume of the final solution. The solution is then placed into 2 ml single dose ampoules.

The above solution is administered to the subject, by injection, once a day at a dose rate of 2 ml per day.

EXAMPLE 3

Controlled Release Oral System

Microcapsules of PD are prepared by spraying PD granules with a solution of carboxymethylene polymers, (such as Carbopol TM 934P) to achieve a coating thickness which will gradually release the PD over an eight hour period.

The above microencapsulated granule are combined in hard gelatin capsules to the extent of 500 mg. PD per capsule.

The composition is administered to the subject at a daily dose rate of 500 mg (i.e., one capsule per day) for two to four weeks.

EXAMPLE 4

Transdermal Release Composition

An admixture was prepared comprising,

|  | Pbw |
| --- | --- |
| Acrylamide copolymer (e.g., Polytrap ® FLME 203) | 20 |
| PD | 5 |
| Alcohol | 74.9 |
| and a fragrance | 0.1 |

The above mixture is applied to the skin, once a day, preferably in the morning, for two to four weeks.

EXAMPLE 5

Tanning Oil

A. An admixture was prepared by adding in the order indicated:

|  | pbw |
| --- | --- |
| decylolcate | 25.0 |
| isopropyl myristate | 15.0 |
| and propylene glycol dicaprylate/dicaprate | 5.0 |
| to mineral oil | 54.85 |

B. An admixture was prepared by adding 0.01 pbw PD to 0.01 pbw of Solertan TM PB-10 (a poly(propylene glycol) lanolyn either.

C. The admixture of part B was added to the admixture of of part A and the resultant admixture mixed until homogeneous.

D. The composition of part C was applied to the skin once or twice daily for two to four weeks.

EXAMPLE 6

Suntanning Lotion

An admixture containing

|  | pbw |
| --- | --- |
| ICI G-1800 (e.g., poly[oxyethylene]21 stearyl ether) | 5.0 |
| isopropyl myristate | 10.0 |
| preservative | 0.1 |
| stearyl alcohol | 2.0 |
| 2-hydroxy -3,3,5,-trimethylhexyl ester of benzoic acid | 8.0 |
| butylated hydroxyanisole | 0.05 |

The above mixture was heated to 70° C. and 60 pbw of water, preheated to 70°, was added thereto. The resultant mixture was stirred and allowed to cool to room temperature.

To the above mixture was then added a 1% citric acid solution, QS, to achieve a pH of 5.0 after which 0.01 pbw of PD was added as well as sufficient deionized water to yield 100 pbw of lotion.

The above lotion is applied to the skin one-half (½) hour prior to exposure to the sun. After swimming, sweating or towelling as well as after each hour of exposure, the lotion is reapplied.

We claim:

1. A composition for increasing melanization in the epidermis of a mammal comprising the admixture of
   (a) an effective amount of at least one O-phosphorylated derivative of DOPA of the formula I

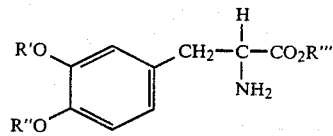

wherein R' and R" each represent hydrogen or

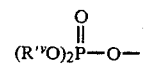

or R' and R" together represent

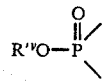

wherein R'ᵛ and R'" each represent hydrogen or a pharmaceutically acceptable cation; with the provisos that R' and R" cannot both be hydrogen and
   (b) a pharmaceutically acceptable carrier.

2. The composition according to claim 1 wherein the O-phosphorylated derivative of DOPA has been prepared from L-DOPA.

3. The composition according to claim 1, wherein said mammal is a human being.

4. The composition according to claim 3, wherein said human being suffers from vitiligo.

5. The composition according to claim 3, wherein said increased melanization imparts a naturally appearing tan to the skin of the human being.

6. The composition according to claim 3 further comprising at least one additive selected from the group consisting of sun screening agents, preservatives, chelating agents, solvents and acidity regulators.

7. The composition according to claim 3, wherein said carrier is a cosmetic base suitable for topical application.

8. The composition according to claim 3, wherein said carrier is a solvent suitable for parenteral administration.

9. The composition according to claim 3 wherein said carrier is suitable for oral administration.

10. The composition according to claim 1 wherein said composition of formula I is

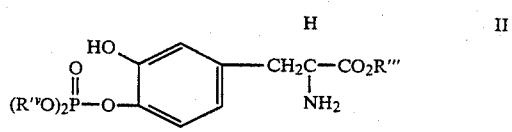

wherein R'" and R'ᵛ are as defined above.

11. The composition according to claim 3 wherein said composition of formula I is

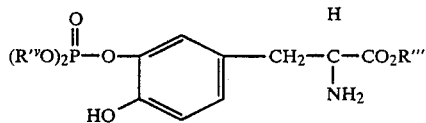 III wherein R''' and R'$^v$ are as defined above.

12. The composition according to claim 3, wherein said composition of formula I is

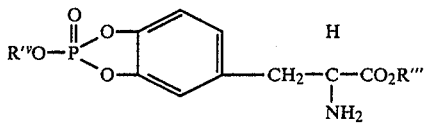 V wherein R''' and R'$^v$ are as defined above.

13. A method for increasing melanization in the epidermis of a mammal comprising the step of administering to the mammal a composition comprising the admixture of (a) an effective amount of at least one O-phosphorylated derivative of DOPA of the formula I

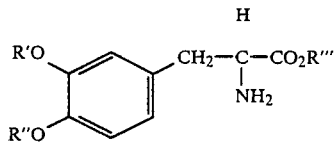

wherein R' and R" each represent hydrogen or

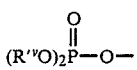

or R' and R" together represent

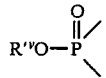

wherein R'$^v$ and R''' each represent hydrogen or a pharmaceutically acceptable cation; with the provisos that R' and R" cannot both be hydrogen and (b) a pharmaceutically acceptable carrier.

14. The method according to claim 13 wherein the O-phosphorylated DOPA derivative has been prepared from L-DOPA.

15. The method according to claim 13, wherein said mammal is a human being.

16. The method according to claim 15, wherein said human suffers from vitiligo.

17. The method according to claim 15, wherein said increased melanization imparts a naturally appearing tan to the skin of the human being.

18. The method according to claim 13 wherein said composition further comprises at least one additive selected from the group consisting of sun screening agents, preservatives, chelating agents, solvents and acidity regulators.

19. The method according to claim 13 further comprising the step of exposing the skin of the mammal to a source of UV radiation during or after administration of the melanization increasing composition for a time sufficient to develop the melanization in said skin.

20. The method according to claim 13, wherein said carrier is a cosmetic base and the composition is administered topically.

21. The method according to claim 20 wherein the composition is administered transdermally.

22. The method according to claim 13, wherein the carrier is a solvent suitable for parenteral administration and the composition is administered parenterally.

23. The method according to claim 13, wherein the composition is administered orally.

* * * * *